Jan. 3, 1956 E. S. BOERNER Plant Pat. 1,446
CHRYSANTHEMUM PLANT
Filed Feb. 15, 1955
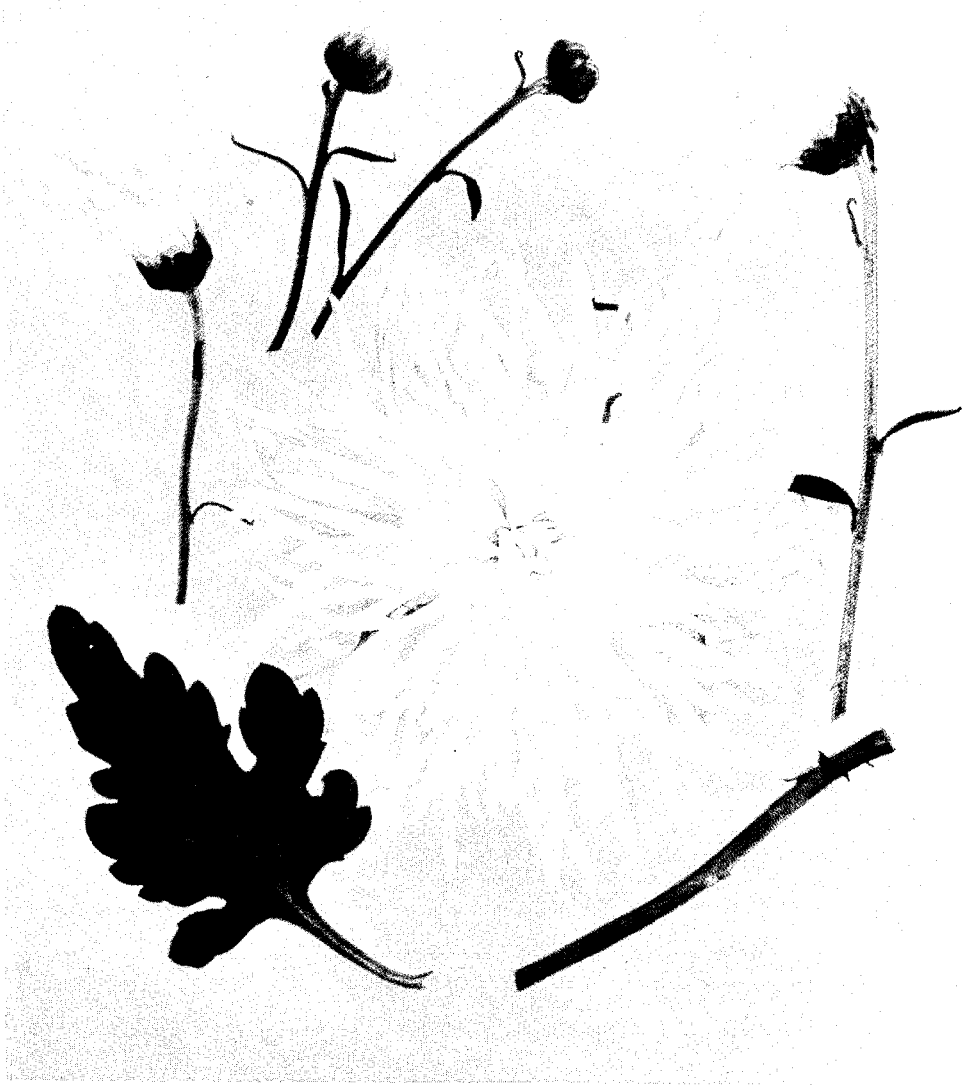
Inventor.
E. S. Boerner
By: Robb & Robb
Attorneys.

United States Patent Office

Plant Pat. 1,446
Patented Jan. 3, 1956

1,446

CHRYSANTHEMUM PLANT

Eugene S. Boerner, Newark, N. Y., assignor to Jackson & Perkins Company, Newark, N. Y., a corporation of New York Application February 15, 1955, Serial No. 488,446

1 Claim. (Cl. 47—60)

The present invention relates to a new and distinct variety of Chrysanthemum plant which was discovered by me as a cultivated sport of the chrysanthemum variety named "Swallow" (Plant Patent No. 1,106), growing in a field of plants under my supervision and control on property of my employer, the assignee of this application, at Newark, New York.

My attention was initially directed to the sport by the distinctively different color of the blooms thereof, which are characterized as Strontian Yellow, lightly overcast with Empire Yellow, in general color tonality, as compared with the Pale Flesh color of the blooms of the parent variety "Swallow." The aforesaid color of the blooms of the sport is new in the chrysanthemum world, and different from the color of any other chrysanthemum variety of which I am aware.

Continued observation of the sport, and asexual reproduction thereof as performed by me by top cuttings and also by underground runners at Newark, New York, have shown and definitely demonstrated that the color characteristic of my new variety comes true to form and is established and transmitted through succeeding propagations. Except for the distinctive color of the blooms, my new variety is substantially identical in all other respects to the parent variety "Swallow."

The accompanying drawing shows typical specimens of the foliage, stems and flowers of my new variety in different stages of development and as depicted in color as nearly true as it is reasonably possible to make the same in a color illustration of this character.

The following is a detailed description of my new variety, with color termniology in accordance with Ridgway's Color Standards and Nomenclature:

Parentage: Sport of the chrysanthemum variety "Swallow."

Classification: Decorative type.

Growth: Upright; clean; attains a height of 24 inches.

Cold resistance: Hardy and does not burn or become injured by frost, as compared with other varieties grown under comparable cultural conditions at Newark, New York.

Blooming period: In the Newark, New York, climatic area, blooming starts about August 30th and continues in profusion until severe freezing temperatures in October or November of the average season.

Bud:

*Color.*—When sepals first divide—Light Green Yellow, Plate 5; when petals begin to unfurl—Pale Greenish Yellow, Plate 5; when half blown: inside—Citron Yellow, Plate 16; outside—Pale Lemon Yellow, Plate 4, with upper half of the petal overcast with Light Cadmium, Plate 4.

*Peduncle.*—Stiff; slender. Color—Parrot Green, Plate 6.

Bloom:

*Size.*—5 inches.

*Stem.*—Normal strength.

*Form.*—Decorative type.

*Petalage.*—Very double.

*Color.*—Center of flower—Pale Lemon Yellow, Plate 4. Outer petals—Citron Yellow, Plate 16. Base of petals—Bright Chalcedony Yellow, Plate 17. Inside of petals—Strontian Yellow, Plate 16, lightly overcast with Empire Yellow, Plate 4. Reverse of petals—Citron Yellow, Plate 16, lightly overcast with Barium Yellow, Plate 16.

Bloom:

*Petals.*—Texture — thick. Form — long; narrow; wavy towards ends of petals.

*Fragrance.*—Slight. Nature—Lemon.

PLANT

Form: Upright; free.

Growth: Free; vigorous.

Foliage:

*Size.*—Large.

*Quantity.*—Normal.

*Color.*—Upper side—Empire Green, Plate 32; reverse side—Hellebore Green, Plate 17.

*Texture.*—Leathery.

I claim:

A new and distinct variety of chrysanthemum plant of the decorative type, substantially as herein shown and described, characterized particularly as to novelty by being substantially identical with the chrysanthemum variety "Swallow" (Plant Patent No. 1,106), except for the new and distinctive Strontian Yellow, lightly overcast with Empire Yellow, general color tonality of its blooms.

No references cited.